United States Patent
Graham et al.

(10) Patent No.: US 7,349,107 B2
(45) Date of Patent: Mar. 25, 2008

(54) SYSTEM AND METHOD FOR CORRECTION FOR ANGULAR SPREAD IN DETERMINING OPTICAL PROPERTIES OF MATERIALS

(75) Inventors: Hsueh-Mei W. Graham, Fort Worth, TX (US); Harris G. Carter, Jr., Fort Worth, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 287 days.

(21) Appl. No.: 10/884,348

(22) Filed: Jul. 2, 2004

(65) Prior Publication Data
US 2005/0006585 A1   Jan. 13, 2005

Related U.S. Application Data

(60) Provisional application No. 60/485,249, filed on Jul. 7, 2003.

(51) Int. Cl.
*G01B 11/289* (2006.01)
(52) U.S. Cl. ..................................................... 356/630
(58) Field of Classification Search ...................... None
See application file for complete search history.

(56) References Cited

U.S. PATENT DOCUMENTS

| | | | |
|---|---|---|---|
| 5,637,873 A | 6/1997 | Davis et al. ........... 250/339.11 |
| 5,895,918 A | 4/1999 | Powell et al. .......... 250/339.08 |
| 5,912,741 A * | 6/1999 | Carter et al. ................. 256/445 |
| 6,297,880 B1 | 10/2001 | Rosenewaig et al. ....... 356/369 |
| 6,381,009 B1 * | 4/2002 | McGahan .................... 356/630 |
| 6,483,590 B1 * | 11/2002 | Davis .......................... 356/445 |
| 6,885,467 B2 * | 4/2005 | Du-Nour et al. ............. 356/630 |
| 6,921,898 B1 * | 7/2005 | Chen ........................... 250/340 |
| 6,982,794 B1 * | 1/2006 | Davis et al. ............ 250/339.11 |
| 7,248,350 B2 * | 7/2007 | Kettler ......................... 356/128 |

FOREIGN PATENT DOCUMENTS

EP   90304800.7   5/1990

OTHER PUBLICATIONS

H. M. Graham, et al., *Correction for Angular Spread in HDR Determination of IR Optical Constants*; SPIE vol. 5192 Optical Diagnostic Methods for Inorganic Materials III; pp. 80-90; 2003.
European Search Report: 3 pp., Nov. 12, 2004.

* cited by examiner

*Primary Examiner*—Gregory J. Toatley, Jr.
*Assistant Examiner*—Juan D Valentin, II
(74) *Attorney, Agent, or Firm*—Bracewell & Giuliani LLP (57) ABSTRACT

The present invention provides a method and system to correct for angular spread within an HDR used to determine IR optical constants. An algorithm simulates the transmission and polarized reflection actually observed. This is achieved by averaging power scattering over an angular spread corresponding to the size of the HDR mirror. Such an algorithm may incorporate corrections for angular spread that may be used to determine the thickness of a film (coating) as well as the optical constants of the film or coating on low loss ranges.

18 Claims, 7 Drawing Sheets

HDR data for Cast Polyethylene of FIG. 3

```
Source temperature = 900°F; wave-number resolution=8 cm⁻¹
Nominal off-normal angle in reflection: θ = 30°
Selected S-pole reflection maximum: ν_s=3642.69 cm⁻¹
R_s(max) = .15842
Average spacing for 2 peaks adjacent to ν_s: (?ν_s)_avg=215.67 cm⁻¹
Transmission minimum nearest ν_s: ν_t=3637.21 cm⁻¹, T(min)=.85066
```

First estimate of n,k,h: Equations (14)-(17)

$n_0=1.411$; $N_s=16$; $h_0=.001716$ cm; $k_0=.00045$

Best-fit procedure for n,k,h: Equations (18)-(24)

```
Search-range of (n,k):    .9n₀ < n < 1.1n₀;  0 < k < 2k₀
Wavenumber-range:         ν_s ± ½(?ν_s)_avg:  3536 < ν_j < 3744 cm⁻¹
Data employed in fit:     ν_j(cm⁻¹), R_sj, T_j, T_j';  1 < j < 28
```

Best-fit results for λ=2.67-2.83μm; half-angle spread due to size of overhead mirror: δ=0°

$n=1.4564$; $k=0.00022$; $h=16.59$ μm; Std. Dev.: $D(n,k) = 1.97\%$

Best-fit results for λ=2.67-2.83 μm; half angle spread due to size of overhead mirror; δ=4°

$n=1.468$; $k=0.00018$; $h=16.41$ μm; Std. Dev.: $D(n,k)=0.49\%$

SYSTEM AND METHOD FOR CORRECTION FOR ANGULAR SPREAD IN DETERMINING OPTICAL PROPERTIES OF MATERIALS

CROSS-REFERENCE TO RELATED APPLICATION

This application claims the benefit of priority to U.S. Provisional Patent Application No. 60/485,249 Entitled "CORRECTION FOR ANGULAR SPREAD IN HDR DETERMINATION OF IR OPTICAL CONSTANTS," filed on Jul. 7, 2003, and is incorporated herein by reference in its entirety.

TECHNICAL FIELD OF THE INVENTION

The present invention relates generally to systems and methods for determining the optical properties of materials. More particularly, the present invention relates to a system and method for correction of angular spread in the determination of IR optical constants using a Hemispherical Directional Reflectometer.

BACKGROUND OF THE INVENTION

Coatings to control infrared reflection and absorption are highly desirable, especially where the emissivity and reflectivity of surfaces are significant features when it relates to detection by optical (infrared ("IR") and visible light) seekers. Coatings are often designed to provide particular emissivity/reflectivity characteristics. However, it is difficult to accurately measure the optical characteristics of these coating material (and hence to design a material for a particular purpose).

Genetic algorithms for design optimizations have made possible a new generation of optical coatings to control infrared reflection and absorption. Configurations suitable for this purpose generally are applied to thick substrates, but otherwise are just IR versions of the Fabry-Perot filter. These configurations incorporate layers, with thicknesses on the order of 1 µm to exploit interference effects. Although an extensive IR-optical data base is now available for design purposes such data for organic materials remains relatively scarce. Tests on thin polymeric films can supply optical properties for design of coatings containing both organic and inorganic layers and also provide useful operational data on the spectro-photometric devices employed.

The Hemispherical Directional Reflectometer (HDR) is a convenient instrument for optical characterization. HDR measurements provide broadband IR data for oblique polarized reflection, as well as normal-incidence transmission. Tests on thin polymer films in low-loss wavelength ranges typically show fringes conforming to Fresnel reflection/transmission. Hence, HDR measurements are a promising approach to determine the optical constants of organic materials. The same experiments also quantify operational features of the HDR for application to inorganic materials.

However, the HDR has some limitations in determining the optical constants of materials. The achievable angular resolution is limited by the HDR configuration. In particular, an overhead mirror used to collect IR radiation scattered from a sample film subtends a non-negligible angle. This effect causes measured reflection extrema to be "damped" relative to rigorous calculations assuming incidence at a discrete angle. Currently existing data-reduction algorithms for deriving the optical constants "n" (refractive index) and "k" (absorptive index) of a material, such as a thin film, do not correct for this observed angular spread. As a result, HDR measurements of the optical constants for a material, as well as for the thickness of the material, lack the accuracy required to develop today's high-tolerance coatings.

Therefore, a need exists for a method and system for correcting angular spread in HDR determination of IR optical constants that can reduce or eliminate the accuracy problems of prior art HDR methods and systems.

BRIEF SUMMARY OF THE INVENTION

The present invention provides a method and system to correct for angular spread in hemispherical directional reflectometer (HDR) determination of infrared "IR" optical constants that substantially addresses the above identified need as well as other needs. Embodiments provide an algorithm operable to simulate the transmission and polarized reflection actually observed (and not corrected for in the prior art). This is achieved by averaging power scattering over an angular spread corresponding to the size of the HDR mirror. Such an algorithm may incorporate corrections for angular spread that may be used to determine the thickness of a film (coating) as well as the optical constants of the film or coating on low loss ranges.

By taking into account the HDR limitations, the embodiments of this invention can use transmission and polarized reflection data provided by an HDR to make accurate estimates of a film's thickness, together with its complex refractive index as a function of wave-length. Corrections demonstrated in work with thin polymeric films may also apply to HDR measurements of optical constants for relatively thick inorganic samples and to critical tests of recent ab initio predictions illustrating the use of software for molecular and solid-state simulation.

Another embodiment provides a method of a film from an HDR measurement. This method includes determining a power transmission and a power reflection coefficient for a uniform film. This data is employed in approximate expressions for power transmission and power reflection, which then yield a first estimate of the IR optical constant near a first wave number. An iterative best-fit search for the IR optical constant is performed. In this operation, an angular spread in off-normal reflection is employed to compensate for the limited angular resolution of the HDR. The resulting simulation supplies a final accurate value for the desired optical constant(s) and film thickness.

The optical constant may include an absorptive index ("k") and/or a refractive index ("n"). The power reflection coefficient may include the S-pole power reflection coefficient and the P-pole power reflection coefficient. The thin films typically have a thickness of about 20 um or less. The first wave number is $v_s$, the wave number for a fringe maximum in S-pole reflection. The method of this invention can also be used to determine the thickness of the film as part of the iterative best-fit search.

Another embodiment provides a particular algorithm apparatus derived to determine IR optical constant of a film from an HDR measurement, and a particular program (HDR . . . nkh). The apparatus may include a processing module and a memory. The processing module may be a single processing device or a plurality of processing devices. The memory can be a single memory device or a plurality of memory devices. The memory stores, and the processing module executes, operational instructions corresponding to at least some of the steps and/or functions of the embodiments of the method of this invention.

BRIEF DESCRIPTION OF THE DRAWINGS

For a more complete understanding of the present invention and the advantages thereof, reference is now made to the following description, taken in conjunction with the accompanying drawings, in which like reference numerals indicate like features and wherein.

DETAILED DESCRIPTION OF THE INVENTION

Preferred embodiments of the present invention are illustrated in the FIGURES, like numerals being used to refer to like and corresponding parts of the various drawings.

Hemispherical Directional Reflectometers ("HDR") provide convenient instruments for optical characterization. Transmission and polarized reflection data provided by an HDR can be used to make accurate estimates of a film's thickness complex refractive index as a function of wavelength. Additionally, corrections of thin polymeric films may also apply to HDR measurements of optical constants for relatively thick inorganic samples.

Figure 1:
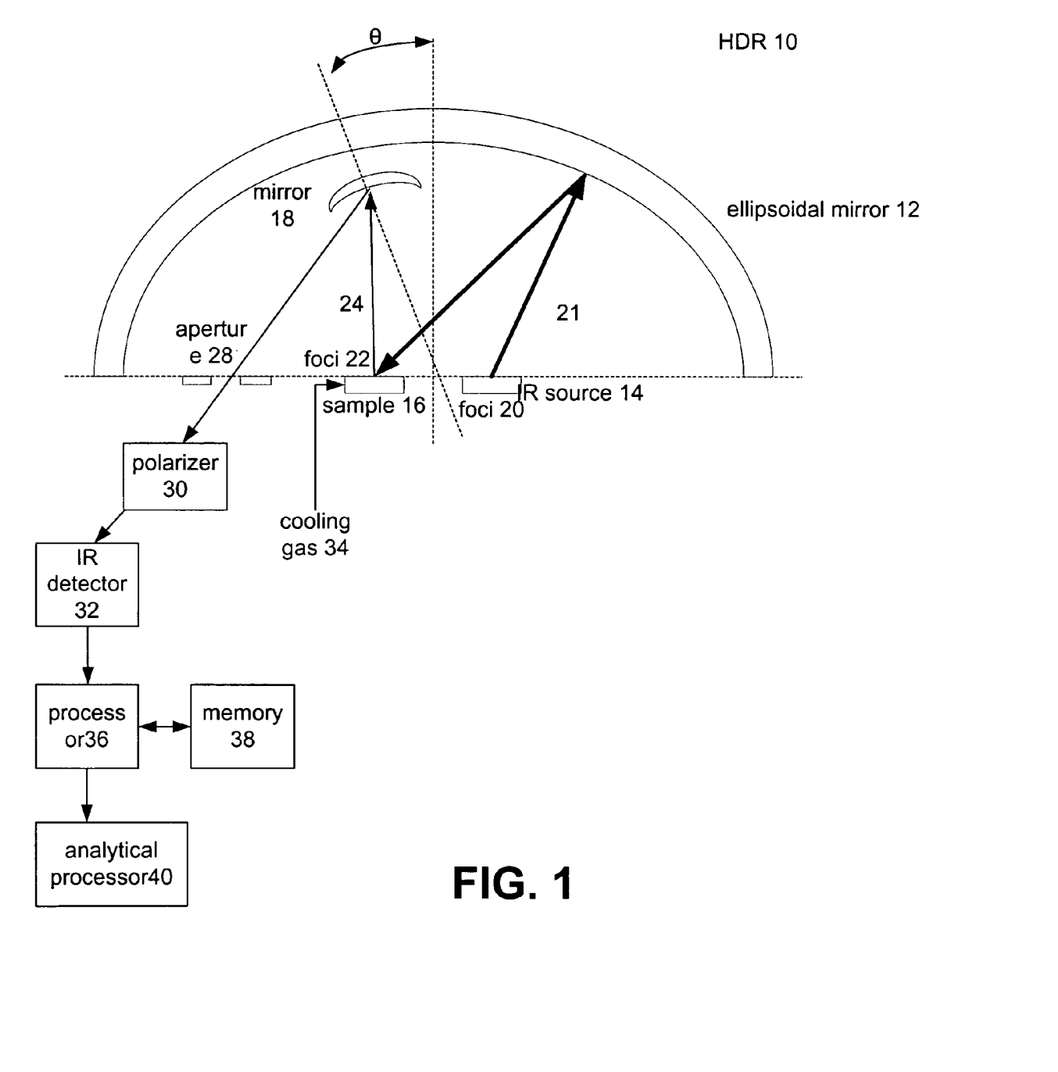
FIG. 1 illustrates the Geometry of an exemplary Hemispherical Directional Reflectometer.

FIG. 1 shows some essential features of the geometry of such an HDR 10. An HDR model SOC-100HDR manufactured by Surface Optics Corporation may be employed in one embodiment. However, the present invention need not be limited to only this HDR. Other similar HDRs may be employed. In this embodiment, a specular-gold coated ellipsoidal dome 12 with short and long axes, acts as a $2\pi$ steradian mirror. Radiation source 14 serves as a source of IR radiation 21. Source 14 is located at one of the two ellipse foci, focal point 20, and can be set to temperatures up to 1300° F. All radiation emitted from the source is first modulated by a chopper, radiated to the ellipsoidal mirror 12 and then uniformly focused from all directions onto sample 16 that rests over a 0.75" sample-cavity at the other focal point, focal point 22. Reflection 24 from sample 16 can then be collected by overhead mirror 18, supported by an arm (not shown) that holds the overhead mirror 18 relative to sample 16. The overhead mirror 18 redirects a portion of the reflected radiation 24 through detector aperture 28. The radiation then passes through polarizer 30 before entering IR detector 32. Transmission is measured simply by collecting radiation 21 that passes through sample 16. A suitable flow of dry nitrogen gas may be used to maintain sample 16 at a constant temperature.

A processor 36 and associated memory 38 are operably coupled to control and process the outputs of HDR 10. Specific processing functions related to the determination of optical properties will be performed by an analytical processor 40 operably coupled to receive the data outputs of the HDR. These functions will be further discussed with reference to FIG. 2.

Processing module 36 and analytical processor 40 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. Memory 38 may be a single memory device or a plurality of memory devices. Such a memory device may be a read-only memory, random access memory, volatile memory, non-volatile memory, static memory, dynamic memory, flash memory, and/or any device that stores digital information. Note that when processing module 36 implements one or more of its functions via a state machine, analog circuitry, digital circuitry, and/or logic circuitry, the memory storing the corresponding operational instructions is embedded with the circuitry comprising the state machine, analog circuitry, digital circuitry, and/or logic circuitry. Memory 38 stores, and processing module 36 executes, operational instructions that may correspond to the steps and/or functions illustrated in FIG. 2 and following.

Specifically, memory 38 operably couples to processing module 36 and includes operational instructions that cause the processing module 36 to determine a power transmission and a power reflection coefficient for a uniform film; approximate the power transmission and the power reflection coefficients for a thin film; determine a first estimate of the IR optical constant near a first wave number; perform an iterative best-fit search for the IR optical constant (as described in greater detail above); and simulate an angular spread in off-normal reflection to compensate for the limited angular resolution of the HDR to obtain a final value for the desired optical constant(s).

HDR measurements of polarized specular reflection are subject to inaccuracies arising from limited wave-number resolution and limited angular resolution. Errors due to the latter effect can be reduced or eliminated by use of an algorithm that takes into account an angular spread determined by the finite diameter of the HDR's overhead mirror. HDR measurements on thin polymeric films provide validation for this correction. For determination of IR optical constants of thin films, angular-spread corrections become increasingly important with increasing optical thickness of the film and increasing off-normal angle.

Figure 2:
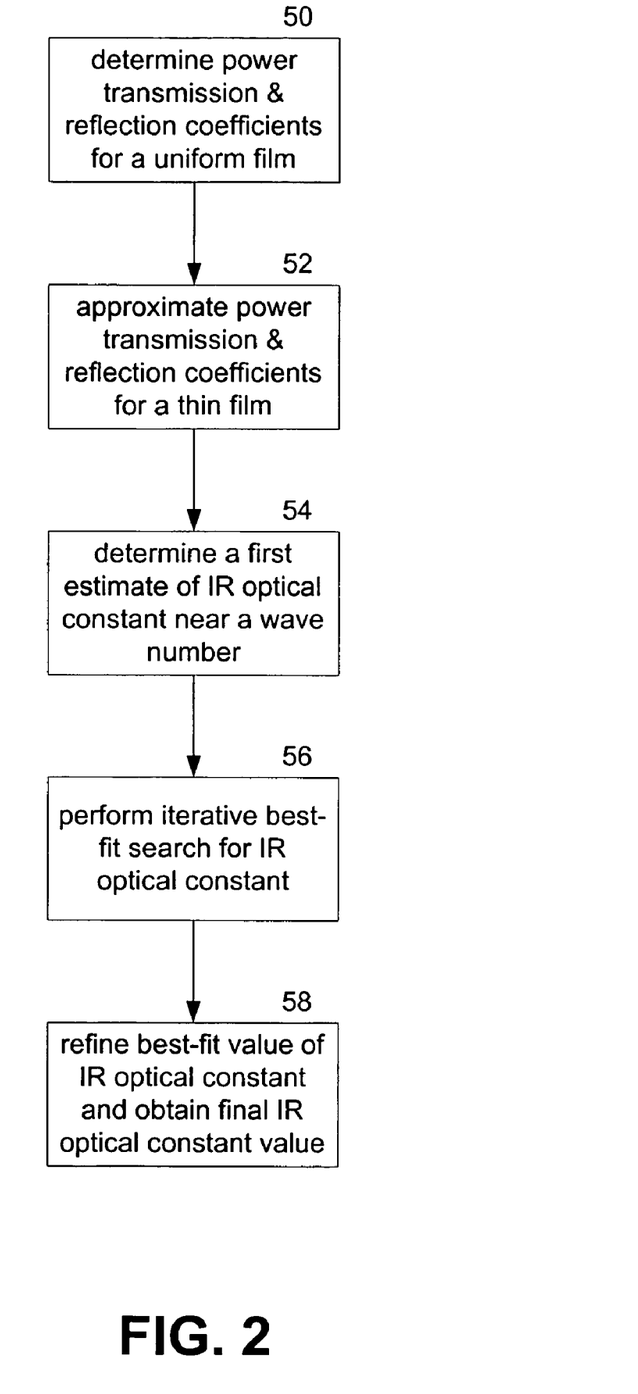
FIG. 2 is a flowchart illustrating the steps of one embodiment of the method of this invention.

The overall method to determine optical properties, such as an IR optical constant of a film from an HDR measurement of this invention is illustrated in the flowchart of FIG. 2. At step 50, a power transmission and a power reflection coefficient are determined for a uniform film. This can be done using Equations (1), (2) and (3) which will be described below. The optical constant may include an absorptive index ("k") and/or a refractive index ("n"). The power reflection coefficient comprises the S-pole power reflection coefficient and the P-pole power reflection coefficient.

Step 52 approximates the power transmission and the power reflection coefficients for a thin film. The thin film typically comprises a film with a thickness of about 20 um or less. In step 54, the method then determines a first estimate of the IR optical constant near a first wave number. The first wave number is $v_s$, the wave number for a fringe maximum in S-pole reflection.

Step 56 performs an iterative best-fit search for the IR optical constant (as previously described in greater detail). Then, step 58 refines the value obtained for the optical constant as part of the best-fit search by simulating an angular spread in off-normal reflection to compensate for the limited angular resolution of the HDR to obtain a final value for the desired optical constant(s). This method can also be used to determine the thickness of the film as part of the iterative best-fit search.

Figure 3:
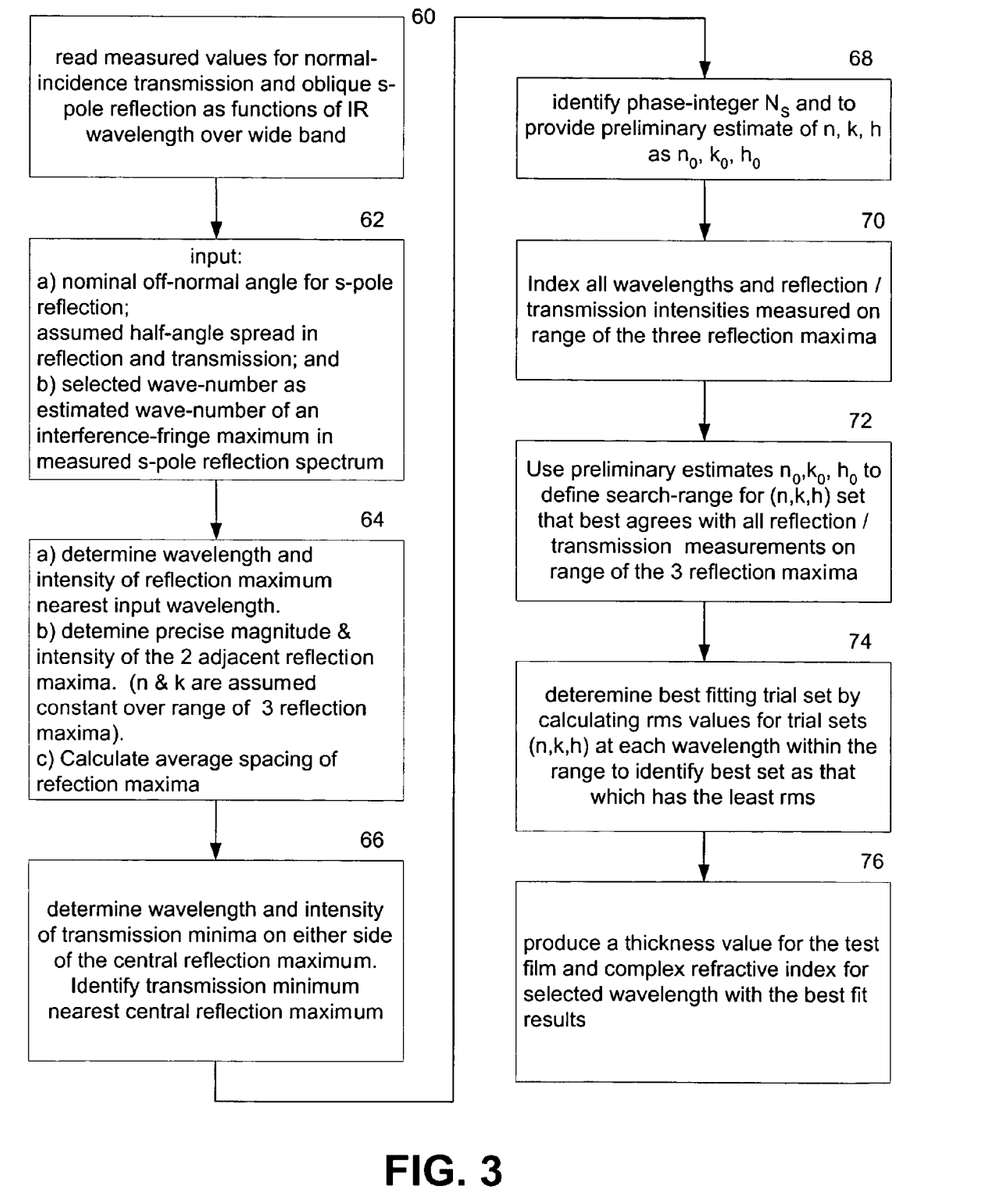
FIG. 3 provides a logic flow diagram of an algorithm that derive the thickness and wavelength-dependent complex refractive index of a thin film from HDR measurements in accordance with one embodiment of the present invention.

Polymeric films with thicknesses on the order of 20 μm make reasonably good samples for exploiting the HDR's capabilities and limitations. FIG. 3 shows data typical of polyethylene, polyvinylidene chloride and other commonplace polymers-films. This graph plots reflection/transmission data as functions of decreasing wave number in $cm^{-1}$. Measured transmission is plotted as % of transmitted power relative to a test with no sample in place. Measured reflection is plotted as % reflected power relative to reflection by a specular gold reference standard.

FIG. 3 provides a logic flow diagram of an algorithm that derive the thickness and wavelength-dependent complex refractive index of a thin film from HDR measurements in accordance with one embodiment of the present invention. The algorithm may be implemented through various programming languages, such as Visual Basic or other like languages known to those skilled in the art and executed within a computing system such as analytical processor 40. The algorithm incorporates a crucial correction for angular spread of IR light impinging on the film. Within FIG. 3, the following symbols and optical constants are defined as follows:

r=n+ik (complex refractive index of a thin film material at infrared wavelength λ);
n=refractive index;
k=absorptive index; and
h=film thickness The equations mentioned in the follow steps will be described later and in further detail.

The algorithm begins with step 60, where measured values for normal-incidence transmission and oblique s-pole reflection as functions of IR wavelength over wide band are read. Then in step 62, the nominal off-normal angle for s-pole reflection, assumed half-angle spread in reflection and transmission, and selected wave-number as estimated wave-number of an interference-fringe maximum in measured s-pole reflection spectrum, are provided as inputs to the algorithm. Step 64 determines the precise wavelength and intensity of reflection maximum nearest input wavelength, as well as the precise magnitude & intensity of the 2 adjacent reflection maxima. Both the refractive index n and absorptive index k are assumed constant over the range of 3 reflection maxima. The wavelength of these maxima allows the average spacing of the reflection maxima to be determined. Step 66 determines the precise wavelength and intensity of transmission minima on either side of the central reflection maximum as well as the transmission minimum nearest central reflection maximum. As will be discussed later, the phase-integer $N_s$ is identified in step 68. Additionally, step 68 provides preliminary estimates of n, k, h as $n_0$, $k_0$, $h_0$ that will be further described with reference to equations 14-17. Step 70 indices all wavelengths and reflection/transmission intensities measured on range of the three reflection maxima determined in step 64. Step 72 uses preliminary estimates $n_0$, $k_0$, $h_0$ to define search-range for (n, k, h) set that best agrees with all reflection/transmission measurements on range of the 3 reflection maxima. Step 74 uses trial sets (n, k, h) over a search range at each wavelength in range. Integrations are performed over angular spread assuming angle-independent distribution due to overhead mirror. If root mean square of any current set is less than that of any prior set, that current set is identified as the best fitting set. Step 76 produces a thickness value for the test film and complex refractive index for selected wavelength with the best fit results. The actual code of one embodiment of this algorithm is provided in Appendix 1.

Figure 4:
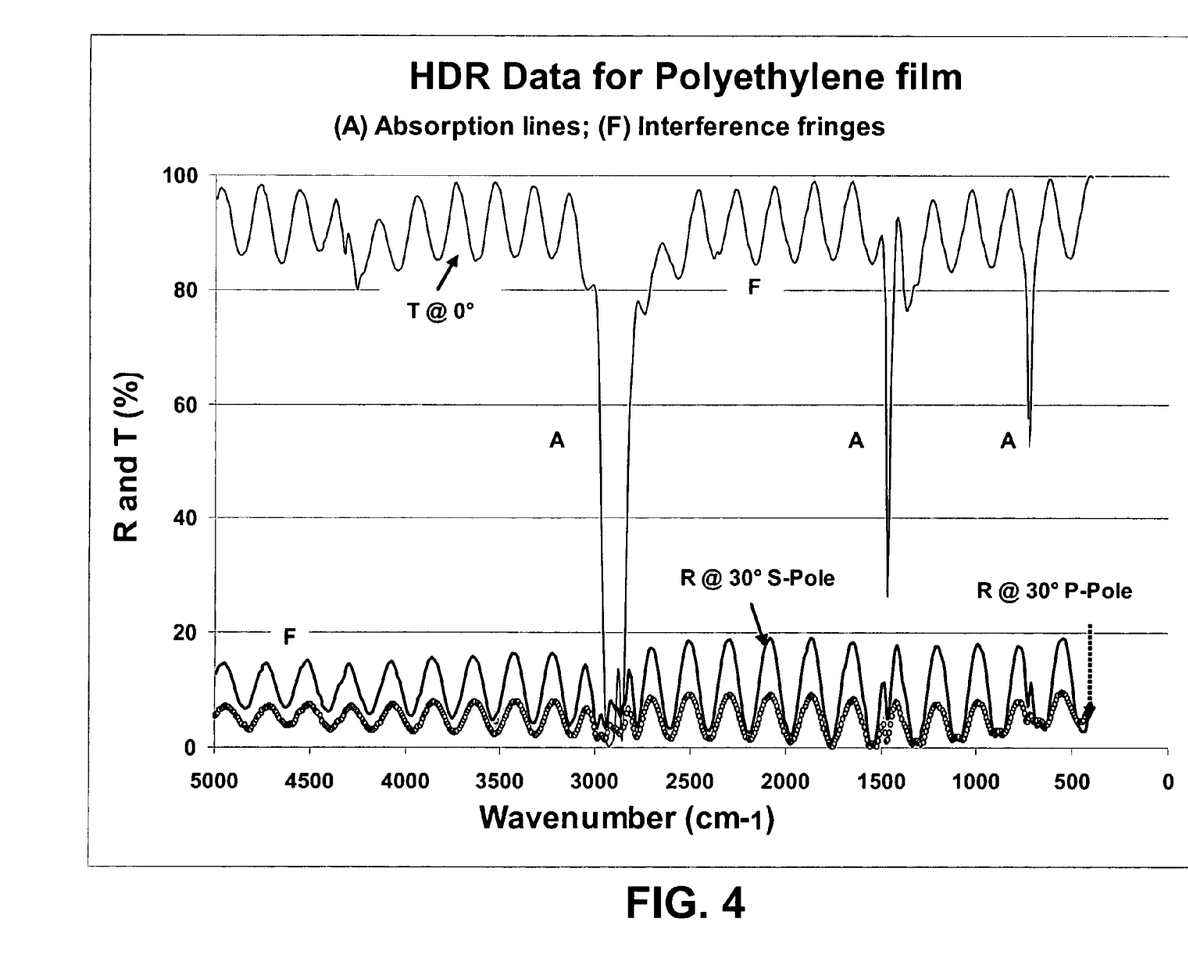
FIG. 4 shows exemplary HDR measurements on a polyethylene film.

The transmission data of FIG. 4 (always taken at normal incidence) show extrema of two types. Sharp minima of the sort labeled "A" are intrinsic absorption features of the material. In the case of polyethylene, these minima are due to IR excitations of internal molecular modes and are characteristic of hydrocarbons including alkenes in both gas and solid form. The first absorption line in FIG. 4 represents a $CH_2$ asymmetric stretch mode at 2926 $cm^{-1}$ and an almost overlapping $CH_2$ symmetric stretch mode at 2855 $cm^{-1}$. The absorption line is due to C—$CH_2$ "scissors mode" at 1455 $cm^{-1}$ A weak absorption line at 1375 $cm^{-1}$ is interpreted as C—CH3 "umbrella mode" due to a residual population of methyl groups. Finally, the sharp line at 720 $cm^{-1}$ is attributed to a C–$CH_2$ "rocking mode".

Repetitive maxima and minima, on the other hand, are interference fringes. In FIG. 4 these are labeled "F" and they appear on the wave-number ranges 5000-4500, 4000-3200, 2500-1600, and 1200-800 $cm^{-1}$. These patterns result from constructive and destructive interference between fields reflected at the upper and lower surfaces of the film. Interference is most pronounced and most regular on bands where n, the refractive index, is independent of wave-number and k, the absorptive index, is weak. Plotted against wave-number $v(cm^{-1})=10000/\lambda(\mu m)$ the extrema are almost evenly spaced. The separation of adjacent extrema decreases with increasing film thickness and increasing refractive index.

FIG. 4 includes HDR reflection data for two extremes of polarization at an off-normal angle of 30°. The strongest reflection occurs in S-polarization (also known as perpendicular polarization), where the incident electric field is fully parallel to the sample-film's surface. In the other extreme case, P-polarization (also called parallel polarization), the magnetic field is fully parallel to the film surface. P-polarization reflection is generally weaker and almost disappears with increasing off-normal angles. Both the S- and P-reflections show well-defined interference extrema on wave-number ranges where the film material's intrinsic absorption is weak.

One implementation is tailored to measure optical constants of films having uniform thickness. In the simplest application, the method applies only to a wave-number range where interference fringes are pronounced and regular. The transmission and S-pole oblique reflection may be used to determine a film's thickness as well as its refractive and absorptive index on ranges where these parameters are approximately constant. This approach provides an alternative to methods based on reflection from thick samples. With thickness established, this methodology can be extended to ranges where the absorptive index is relatively high and optical constants vary strongly with wave-number. Modifications for this purpose can employ Kramers-Kronig analyses or various analytical forms that have been used as a means of deriving dispersive n, k spectra from broadband spectrophotometric data.

The following symbols are convenient for use with the embodiments of the optical constants algorithm of this invention and indicate some of the approach and assumptions employed here.

θ=nominal off-normal angle in HDR reflection measurement

δ=half-angle subtended by overhead mirror at sample position

ν=wave-number [(wavelength=λμm)=10000/ν(cm$^{-1}$)]

T=normal-incidence power transmission coefficient (expressed as a fraction)

$R_s$, $R_p$=power coefficients (fractions) for S-pole, P-pole reflection at θ

$\nu_s$=ν for fringe maximum in S-pole reflection $R_s$(max)=$R_s(\nu_S)$=peak value of power coefficient for S-pole reflection at θ

$(\Delta\nu_s)_{avg}$=average separation of maxima in S-pole reflection in vicinity of $\nu_s$ $\nu_t$=wave-number for fringe minimum in normal transmission T(min)=T($\nu_t$)=normal-incidence power transmission minimum at $\nu_t$ h=film thickness φ=2πhν n=refractive index, K=absorptive index r=n+ik=complex refraction index $r_\theta=(r^2-\sin^2\theta)^{1/2}$ Interference fringes appearing in HDR measurements are coherent effects that are described most generally in terms of complex transmission and reflection coefficients for plane-wave incidence on layered media. In the case of a single homogeneous layer with arbitrary n, k, h, the corresponding power coefficients for normal-incidence transmission and polarized oblique reflection assume the following relatively simple forms:

$$T = \left| \frac{2r}{2r\cos\varphi r - i(r^2+1)\sin\varphi r} \right| \quad (1)$$

$$R_s = \left| \frac{(r^2-1)\sin\varphi r_\theta}{2(\cos\theta)r_\theta \cos\varphi r_\theta - i(r_\theta^2+\cos^2\theta)\sin\varphi r_\theta} \right|^2 \quad (2)$$

$$R_P = \left| \frac{(r_\theta^2-r^4\cos^2\theta)\sin\varphi r_\theta}{2(\cos\theta)r^2 r_\theta \cos\varphi r_\theta - i(r^4\cos^2\theta+r_\theta^2)\sin\varphi r_\theta} \right|^2 \quad (3)$$

In the special case where k=0, the above relations conform to Fresnel's equations for reflection and refraction at a boundary. The interference fringes in FIG. 4 are slightly attenuated versions of interference patterns for k=0.

Films suitable for elucidation of IR characteristics are assumed to have thicknesses on the order of 20 μm or less, and to have absorptive indices of no more than about K=0.003 on wave-number ranges where pronounced and evenly spaced interference patterns appear in HDR data. Under these conditions the inequality:

$$k\phi \ll 1 \quad (4)$$

provides at least a valid starting point for iterative evaluation of optical constants on the IR range of wave-numbers below 5000 cm$^{-1}$ (wavelengths above 2 μm). To the extent that Equation (4) holds, Equation (1) satisfies the approximation $$T \approx \frac{4}{y^2-(y^2-4)\cos^2\varphi n} - \frac{16\varphi ky}{[y^2-(y^2-4)\cos^2\varphi n]^2}; y \equiv n+n^{-1} \quad (5)$$

The transmission minima fall at ν=$\nu_t$ for which $\cos^2\phi n=0$. Thus, $$\nu_T=(N+1/2)/2hn; N=0,1,2,\ldots \quad (6)$$

and the corresponding transmission coefficients are given by $$T_{(min)}=T(\nu_T)\approx 1-8\pi h\nu_T k(n+n^{-1}); \quad (7)$$

When Equation (4) is satisfied and consideration of HDR results for S-pole reflection is confined to wave-numbers in the vicinity of observed extrema, it is generally sufficient to start with a no-loss (k=0) version of the expression for S-pole reflection. Substitution of k=0 into Equation (2) yields.

$$Rs = \frac{(n^2-1)^2\sin^2\varphi r_\theta}{4r_\theta^2\cos^2\theta+(n^2-1)^2\sin^2\varphi r_\theta}; r_\theta \approx \sqrt{n^2-\sin^2\theta} \quad (8)$$

Analysis of Equation (8) shows that the S-pole reflection extrema are located as follows:

$$R_s \text{ min}: \phi r_\theta=N\pi; N=0,1,2,\ldots \quad (9)$$

$$R_s \text{ max}: \phi r_\theta=\pi/2+N\pi; N=0,1,2,\ldots \quad (10)$$

Then according to Equation(8), the S-pole minima are actually reflection nulls ($R_s$=0), and values for the S-pole reflection maxima are approximated as $$R_s(\text{max}) \approx \left[\frac{n^2-1}{n^2+\cos 2\theta}\right]^2 \quad (11)$$

These reflection peaks are located at:

$$\nu_s = \frac{N+1/2}{2h\sqrt{n^2-\sin^2\theta}}; N=0,1,2,\ldots \quad (12)$$

and are separated by wave-number increments $$\Delta\nu_s = \frac{1}{2h\sqrt{n^2-\sin^2\theta}} \quad (13)$$

Comparison of Equations (6) and (12) shows that, except where the off-normal reflection angle is θ=0, the selected reflection maximum at $\nu_s$ won't coincide with a normal-incidence transmission minimum. The distance between $\nu_s$ and a transmission minimum at $\nu_t$, however, is never more than about ½$(\Delta\nu_s)_{avg}$. Accordingly, the embodiments of the algorithm of this invention assume that n is constant on the range $\nu_s \pm \frac{1}{2}(\Delta\nu_s)_{avg}$ and use both reflection and transmission data on this range.

The following embodiment of the algorithm according to the teachings of this invention refers to values of n and k near the particular wave-number $\nu=\nu_s$ and employs rearrangements of Equations (11), (13), (12) and (7) in that order. Subscripts "0" indicate preliminary estimates. The correct integer Ns for S-pole reflection is determined by rounding a real number to the nearest integer.

$$n_0 = \sqrt{\frac{1 + \sqrt{R_s(\max)}\cos 2\theta}{1 - \sqrt{R_s(\max)}}} \tag{14}$$

$$N_S = \text{Round}\left[\frac{\nu_S}{(\Delta\nu_S)_{av}} - \frac{1}{2}\right] \tag{15}$$

$$h_0 = \frac{N_s + 1/2}{2\nu_s\sqrt{n_0^2 - \sin^2\theta}} \tag{16}$$

$$k_0 = \frac{1 - T(\min)}{8\pi\nu_T h(n_0 + n_0^{-1})} \tag{17}$$

In Equation (17), $T_{(min)}$ is the transmission minimum $T(\nu_t)$ lying nearest the selected S-pole reflection maximum at $\nu_s$.

It can be shown that Equation (16), which only involves the position of a selected reflection maximum and not its magnitude, holds to a good approximation even when the product $k\phi$ is too large to satisfy Equation (4) or when the exact value of the maximum is not well resolved. Hence, Equation (16), in addition to providing a preliminary estimate of thickness, provides an accurate value of the thickness h corresponding to any trial value of n. Thus, an iterative solution for (n, k, h) can be achieved by a numerical 2-dimensional search on a small range of (n, k) space. This search starts with (n, k) first-estimates calculated by using Equations (14)-(17), employs Equation (16) to determine h for each trial value of n, and tests trial sets (n, k, h) by applying the rigorous transmission/reflection relations of Equations (1) and (2) to HDR data on the range of $\nu_s \pm \frac{1}{2}(\Delta\nu_s)_{avg}$.

Selection of the set (n, k, h) that best represents the film near $\nu_s$ according to the general relations of Equations (1) and (2) is based on root-mean-square deviations of calculated values of T(%) and $R_s$ (%) from HDR data at measurement points inside the interval of width $(\Delta\nu_s)_{avg}$. With the HDR wave-number resolution set for 8cm$^{-1}$ the best-fit search for a set (n, k, h) draws upon approximately 25 measured reflection points ($\nu$, $R_s$) and 25 measured transmission points ($\nu$, T). Validation of the results is achieved by applying Equation (2) at another off-normal angle, or by applying Equation(3) to test calculated results against measurements for P-pole reflection.

Application of this procedure reveals the address of the extrema appearing in off-normal reflection measurements being damped due to the finite resolution of the overhead mirror 18. Rays incident at a nominal off-normal angle θ actually have a spread of ±5° or so about the nominal value. Analyses show that this effect has negligible impact on normal-incidence measurements of T(%) and also produces no significant shift in the positions of the oblique-incidence reflection extrema as far as Equation (12) is concerned. However, the finite angular resolution translates into fairly significant errors in magnitudes of $R_s$(%) and $R_p$(%) at off-normal angles greater than about θ=30°. The effect is particularly noticeable in the way of off-normal reflection minima that don't approach 0 even in cases where Equation (17) indicates that k is very small. As a result of the imperfect angular resolution, this procedure of securing a best fit with rigorous reflection expressions may yield (n, k, h) results that are no better than the initial estimates.

Compensation for imperfect angular resolution can be achieved by factoring the effect of a known angular spread into the numerical search to determine (n, k, h). With this angular spread assumed to be uniform, the S-pole power-reflection coefficient at each experimental wave-number $\nu_i$ in the interval $(\Delta\nu_s)_{avg}$ is simulated by the average $$\langle R_s(\nu_i)\rangle = \frac{1}{2\delta}\int_{\theta-\delta}^{\theta+\delta} R_s(\nu_i, \theta')d\theta' \tag{18}$$

where δ is the half angle spread due to the overhead mirror 18 and $R_s(\nu_i, \theta';)$ is given by Equation (2).

Even though angular spread has little effect on HDR data for normal-incidence transmission, instead of Equation (1), this algorithm may employ rigorous oblique incidence transmission relations to determine angular averages. The formula for this purpose is $$\langle T(\nu_i)\rangle = \frac{1}{4\delta}\int_{-\delta}^{+\delta}[T_s(\nu_i, \theta') + T_p(\nu_i(\theta')]d\theta' \tag{19}$$

where, in analogy to Equations (2) and (3), $$T_s = \left|\frac{2(\cos\theta)r_\theta}{2(\cos\theta)r_\theta\cos\varphi_\theta - i(r_\theta^2 + \cos^2\theta)\sin\varphi_\theta}\right|^2 \text{ and} \tag{20}$$

$$T_p = \left|\frac{2(\cos\theta)r^2 r_\theta}{2(\cos\theta)r^2 r_\theta\cos\varphi_\theta - i(r_\theta^4\cos^2\theta + r_\theta^2)\sin\varphi_\theta}\right|^2 \tag{21}$$

are general expressions for S-pole and P-pole power transmission through a single layer. Finally, for comparisons, angular averages for P-pole reflection are calculated as $$\langle R_p(\nu_i)\rangle = \frac{1}{2\delta}\int_{-\delta}^{+\delta} R_p(\nu_i, \theta')d\theta' \tag{22}$$

The averages prescribed in Equations (18), (19) and (22) may be determined by numerical integration.

For each trial combination (n, k) considered, thickness h is accurately approximated by the k-independent form indicated in Equation (16):

$$h = \frac{N_s + 1/2}{2\nu_s\sqrt{n^2 - \sin^2\theta}} \tag{23}$$

With n, k, h fixed, Equations (18) and (19) are then evaluated at each experimental point $\nu_i$ in the selected wave-number range about $\nu_s$. A standard deviation for J pairs of measured values $R_{sj}$ and $T_j$ is calculated as $$D(n, k) = \tag{24}$$

$$\frac{1}{\sqrt{2(J-1)}}\left[\sum_{j=1}^{J}(\langle R_s(\nu_j)\rangle - R_{Sj})^2 + (\langle T(\nu_j)\rangle - T_j)^2\right]^{1/2}$$

The D(n, k) are used to identify a trial set (n, k, h) that produces the least standard deviation from the measured results.

The analytical procedure described above essentially provides a way to interpret local interference fringes. This method supplies a film thickness h along with the optical constants n and k for the film on a narrow range of wave-numbers. The algorithm's validity requires a film-sample whose thickness is uniform over the sample-cavity diameter. Cast films manufactured for use in optical filters and similar purposes may present thickness variations from one place to the next. Although micrometer measurements are not reliable for determining the absolute thickness of thin films, they are an effective means of selecting a relatively uniform sample. Non-uniform samples can also sometimes be identified and rejected on the basis of anomalies discerned in the measured power transmission extrema at IR wavelengths. When thickness variations in the film-stock are expected, it is important to use the same sample for reflection and transmission tests.

Application of the (n, k, h) algorithm is useful for IR wavelength ranges where regularity of interference fringes in the HDR data indicates that k is low and both n and k are approximately independent of wavelength. Applications to a variety of polymer films with thicknesses ranging from 10 to 30 um show that this condition is usually met at one or more places in spectra extending from 2 to 20 μm. The smallest deviations D(n, k) are attained by assuming an effective half-angle spread of δ=4° rather than the nominal δ=5°.

The HDR measurements of FIG. 4 were made on a sample cut from a roll of commercially available cast polyethylene film. The film's degree of crystallinity was not experimentally determined, but is presumed to be in the range of 50%-80%. Film temperature during HDR runs is about 32° C. for typical nitrogen flow rates. The Table provided in FIG. 5 provides summarizes the application of the algorithm to interference patterns on a sub-range from 2.67 to 2.83 μm.

Figure 5:
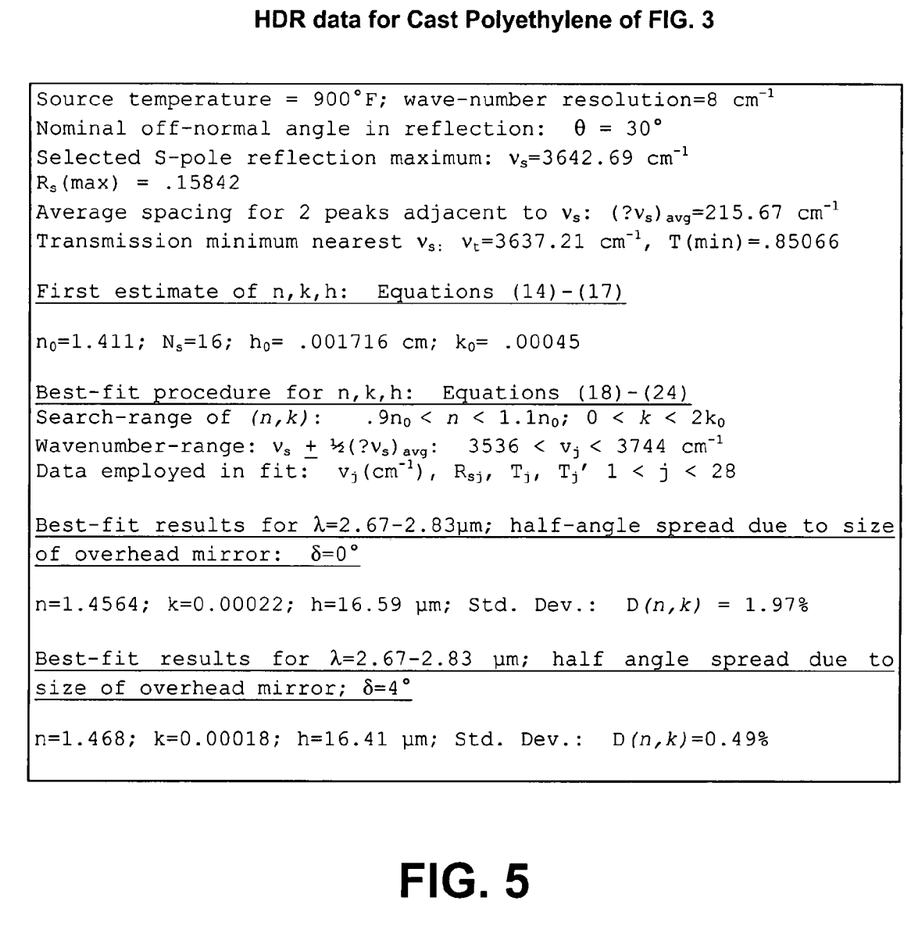
FIG. 5 indicates the nature of corrections for angular spread in film characterization.
Figure 6:
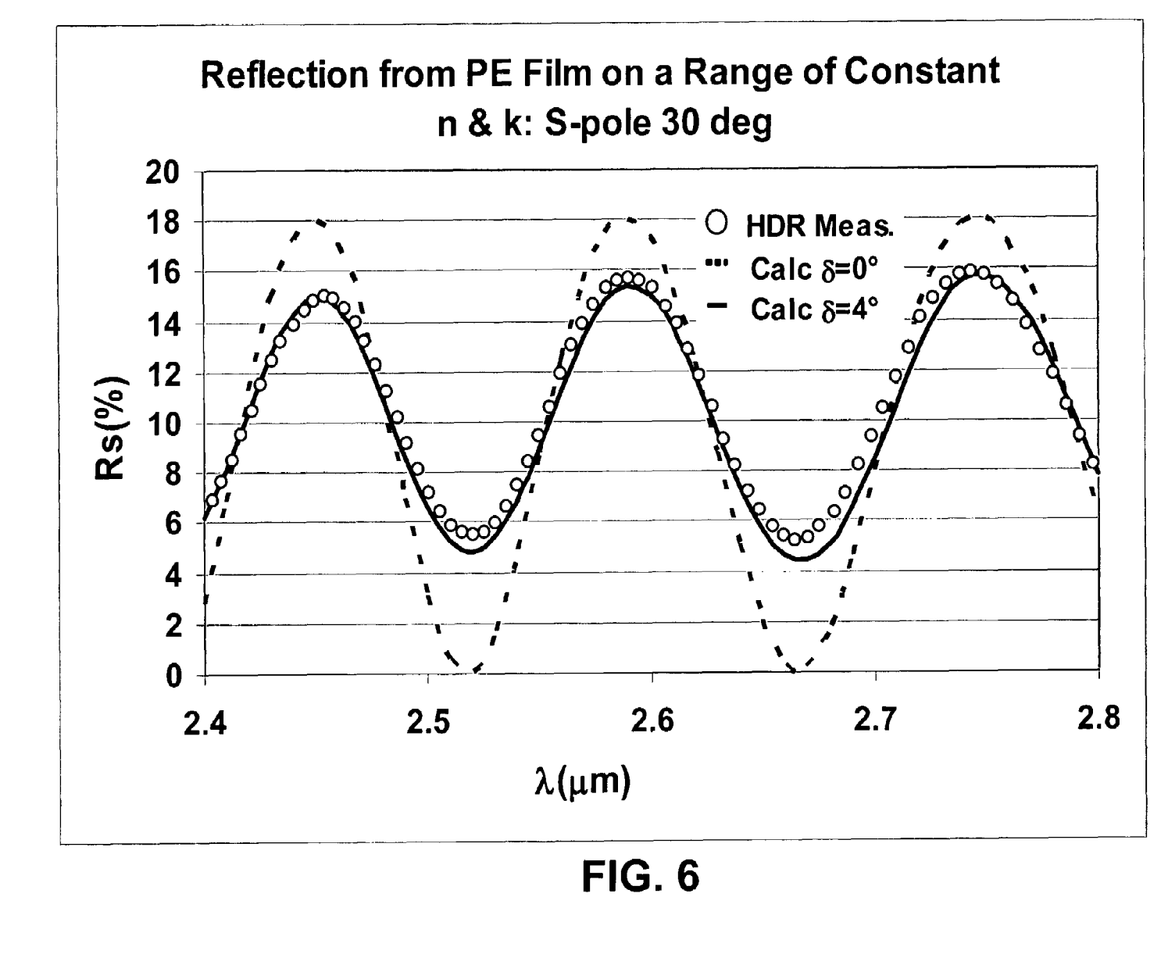
FIG. 6 illustrates overall conformity of HDR measurements to (n,k,h) results based on δ=4.

FIG. 5 indicates the nature of corrections for angular spread in film characterization. In this case, (n, k, h) results for δ=0° and δ=4°, averaged over two adjacent sub-ranges, labeled (a) and (b) in Table 2 below, were used to calculate S-pole reflection θ=30°. Extrema of the calculations for δ=4°, in agreement with HDR measurements, are damped relative to calculations for a discrete off-normal angle. In FIGS. 5 and 6, HDR measurements and calculations are shown as a function of wavelength instead of wave-number.

Figure 7:
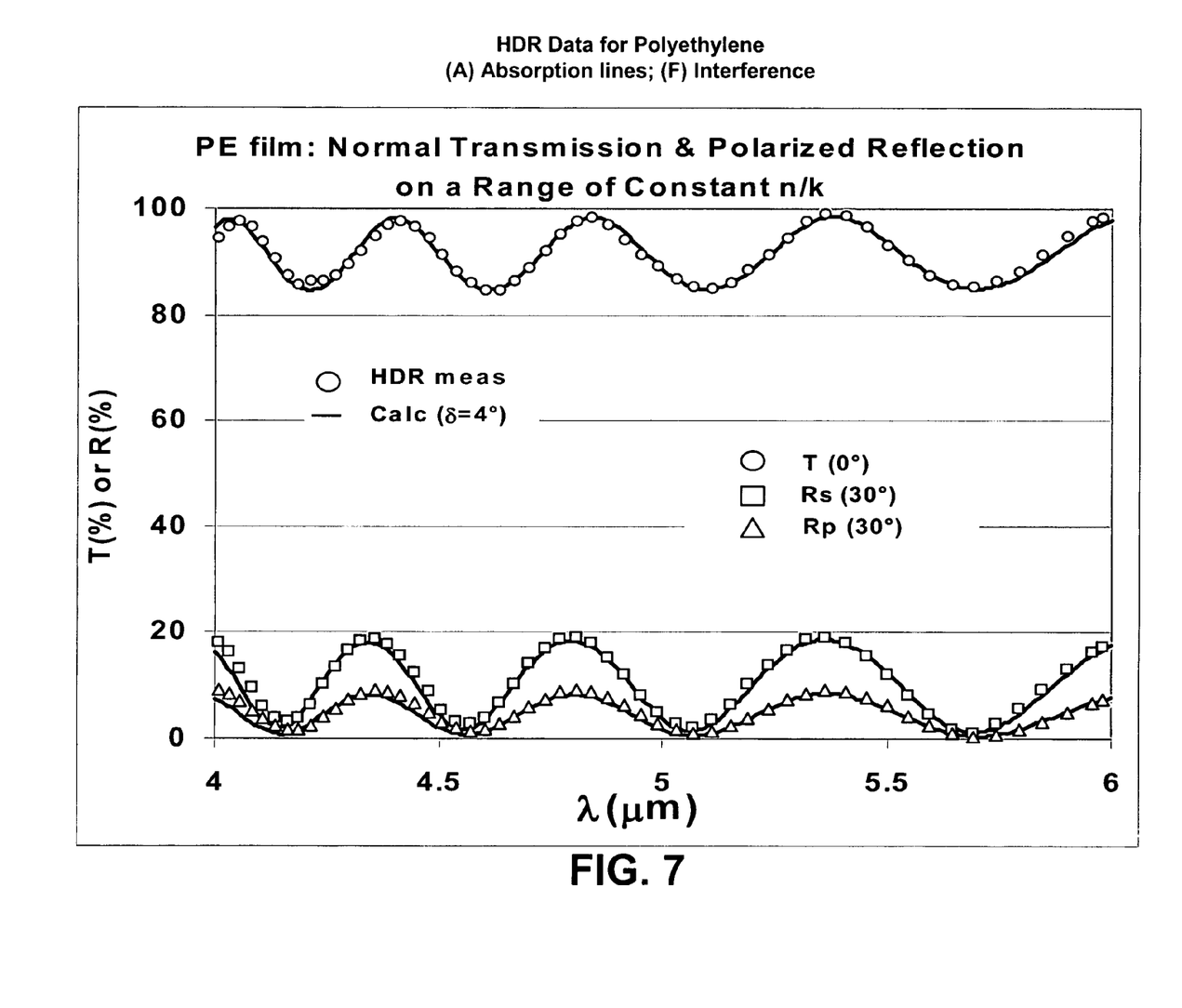
FIG. 7 illustrates overall conformity of HDR measurements to (n,k,h) results based on δ=4

Angular spread has a significant effect on (n, k, h) output for the particular off-normal angle, film-thickness and wavelength range considered in FIG. 6 and FIG. 7, but becomes less important at longer wavelengths. More generally, as long as interference patterns are strong the corrections required to account for the finite size of the overhead mirror rise with increasing off-normal angle and with increasing values of n, h, v—the film's thickness expressed in internal wavelengths. On the other hand, analyses indicate that effects of angular spread on reflection from homogeneous semi-infinite media with smooth surfaces are usually not pronounced.

FIG. 8 illustrates overall conformity of HDR measurements to (n, k, h) results based on δ=4°. These calculations used (n, k, h) averages over three adjacent sub-ranges, labeled (c), (d) and (e) in Table 1, where n and k are approximately constant. The calculated curves for normal-incidence transmission and polarized reflection at 30° off-normal practically overlay the measurements. In the case of T(%) and $R_s$(%), which are employed by the thin-film algorithm, the agreement simply amounts to a good fit. On the other hand the satisfactory agreement between measured and calculated $R_p$(%) is evidence of the validity of this method.

A more stringent critical test of the thin-film algorithm of this invention for determination of (n, k, h) refers to agreement among sample thicknesses that the algorithm returns to different sub-ranges of IR wavelength. Table 1 summarizes results for selected sub-ranges of the HDR data shown in FIG. 7. The remarkably narrow thickness variation, about 0.1 μm, attests to the accuracy of the algorithm.

TABLE 1

| sub-range | λ (μm)    | n     | k      | h (μm) |
|-----------|-----------|-------|--------|--------|
| (a)       | 2.53-2.67 | 1.478 | .00030 | 16.30  |
| (b)       | 2.67-3.83 | 1.468 | 000018 | 16.41  |
| (c)       | 4.16-4.35 | 1.479 | .00039 | 16.41  |
| (d)       | 4.57-5.05 | 1.485 | .00040 | 16.30  |
| (e)       | 5.07-5.65 | 1.486 | .00028 | 16.37  |
| (f)       | 5.67-9.15 | 1.467 | .00154 | 16.45  |

The absorption indices k shown in Table 1 is appreciably lower than values given in a recent comprehensive review of optical constants for polyethylene. J. Ashok, P. L. H. Varaprasad & J. R. Birch, "Polyethylene $(C_2H_4)_N$", *Handbook of Optical Constants of Solids*, (E. D. Palik & G. Ghosh, Eds.), Vol. 2; 957, Academic Press, 1998 which is hereby incorporated by reference. Those authors assumed n=1.5 for the whole mid-IR range and analyzed previously-reported transmission data for three thick samples of a polyethylene called Marlex 50. The present results for k are 60-80% lower on the 2.53-2.83 um range and 20%-50% lower at longer wavelengths. This disagreement may be due in part to chemical differences. It can also be conjectured that the two types of polyethylene differ in regard to relatively weak phonon mechanisms for IR absorption in wave-length ranges between strong molecular absorption lines.

Aside from constraints on k and h implied by Equation (4), application of the thin-film algorithm of this invention on the SOC-100HDR is limited by the SOC-100HDR system's resolution-limit of 8 cm$^{-1}$. A polymeric film 50 μm thick, for example, would produce reflection/transmission extrema too close together to allow an accurate characterization by the method of this invention on the SOC-100HDR. On the other hand, simulations of applications to typical polymeric films thinner than 20 μm indicate that errors due to wave-number resolution are small.

In summary, the present invention provides a method and system to correct for angular spread within an HDR used to determine IR optical constants. An algorithm simulates the transmission and polarized reflection actually observed. This is achieved by averaging power scattering over an angular spread corresponding to the size of the HDR mirror. Such an algorithm may incorporate corrections for angular spread that may be used to determine the thickness of a film (coating) as well as the optical constants of the film or coating on low loss ranges.

By taking into account the HDR limitations, the embodiments of this invention can use transmission and polarized reflection data provided by an HDR to make accurate estimates of a film's thickness, together with its complex refractive index as a function of wave-length. Corrections demonstrated in work with thin polymeric films may also apply to HDR measurements of optical constants for relatively thick inorganic samples and to critical tests of recent ab initio predictions illustrating the use of software for molecular and solid-state simulation.

Although the present invention is described in detail, it should be understood that various changes, substitutions and alterations can be made hereto without departing from the spirit and scope of the invention as described.

What is claimed is:

1. A method for determining an Infrared ("IR") optical constant of a film from a Hemispherical Directional Reflectometer ("HDR") measurement, comprising:
   determining a power transmission and a power reflection coefficient for a uniform film;
   approximating the power transmission and the power reflection coefficients for a thin film;
   determining a first estimate of the IR optical constant near a first wave number;
   performing an iterative best-fit search for the IR optical constant; and
   simulating an angular spread in off-normal reflection to compensate for angular resolution of the HDR to obtain a final value for the optical constant.

2. The method of claim 1, further comprising determining the thickness of the film.

3. The method of claim 1, wherein the optical constant comprises at least one of an absorptive index ("k") and a refractive index ("n").

4. The method of claim 1, wherein the thin film comprises a film with a thickness of about 20 um or less.

5. The method of claim 1, wherein the power reflection coefficient comprises at least one of S-pole power reflection coefficient and P-pole power reflection coefficient.

6. The method of claim 1, wherein the first wave number is the wave number for a fringe maximum in S-pole reflection.

7. The method of claim 1, wherein the optical constant comprises an absorptive index ("k") and a refractive index ("n") and wherein performing an iterative best-fit search comprises a two-dimensional search on a predetermined small range of n and k values, starting with the value of n and k determined in the determining a first estimate step.

8. The method of claim 1, wherein the simulated angular spread is a uniform angular spread.

9. The method of claim 1, wherein the HDR is a model SOC-100HDR manufactured by Surface Optics Corporation.

10. An apparatus for determining an Infrared ("IR") optical constant of a him from a Hemispherical Directional Reflectometer ("HDR") measurement, the apparatus comprising:
    a processing module; and
    a memory operably coupled to the processing module, wherein the memory includes operational instructions that cause the processing module to:
    determine a power transmission and a power reflection coefficient for a uniform film;
    approximate the power transmission and the power reflection coefficients for a thin film;
    determine a first estimate of the IR optical constant near a first wave number;
    perform an iterative best-fit search for the IR optical constant; and
    simulate an angular spread in off-normal reflection to compensate for angular resolution of the HDR to obtain a final value for the optical constant.

11. The apparatus of claim 10, further comprising operational instructions that cause the processing module to determine the thickness of the film.

12. The apparatus of claim 10, wherein the optical constant comprises at least one of an absorptive index ("k") and a refractive index ("n").

13. The apparatus of claim 10, wherein the thin film comprises a film with a thickness of about 20 um or less.

14. The apparatus of claim 10, wherein the power reflection coefficient comprises at least one of S-pole power reflection coefficient and P-pole power reflection coefficient.

15. The apparatus of claim 10, wherein the first wave number is the wave number for a fringe maximum in S-pole reflection.

16. The apparatus of claim 10, wherein the optical constant comprises an absorptive index ("k") and a refractive index ("n") and wherein performing an iterative best-fit search comprises a two-dimensional search on a predetermined small range of n and k values, starting with the first estimate value of n and k.

17. The apparatus of claim 10, wherein the simulated angular spread is a uniform angular spread.

18. The apparatus of claim 10, wherein the HDR is a model SOC-100HDR manufactured by Surface Optics Corporation.

* * * * *